(12) United States Patent
Hopen, Sr. et al.

(10) Patent No.: US 11,152,093 B1
(45) Date of Patent: Oct. 19, 2021

(54) MEDICATION ADHERENCE METHOD AND APPARATUS

(71) Applicant: GuardianMedTech, LLC, Oldsmar, FL (US)

(72) Inventors: Anton J. Hopen, Sr., Palm Harbor, FL (US); Anna Noel Hopen, Palm Harbor, FL (US)

(73) Assignee: Guardianmedtech, LLC, Oldsmar, FL (US)

( * ) Notice: Subject to any disclaimer, the term of this patent is extended or adjusted under 35 U.S.C. 154(b) by 0 days.

(21) Appl. No.: 17/240,500

(22) Filed: Apr. 26, 2021

Related U.S. Application Data

(63) Continuation-in-part of application No. 17/074,927, filed on Oct. 20, 2020, now Pat. No. 11,017,893, which is a continuation of application No. 16/558,746, filed on Sep. 3, 2019, now Pat. No. 10,825,559.

(51) Int. Cl.
| | |
|---|---|
| *G16H 20/10* | (2018.01) |
| *G06K 7/14* | (2006.01) |
| *A61J 1/03* | (2006.01) |
| *A61J 7/04* | (2006.01) |

(52) U.S. Cl.
CPC ............ *G16H 20/10* (2018.01); *A61J 1/03* (2013.01); *A61J 7/04* (2013.01); *G06K 7/1417* (2013.01); *A61J 2200/30* (2013.01); *A61J 2205/10* (2013.01)

(58) Field of Classification Search
CPC ......... G16H 20/10; G06K 7/1417; A61J 1/03; A61J 7/04; A61J 2200/30; A61J 2205/10
See application file for complete search history.

(56) References Cited

U.S. PATENT DOCUMENTS

| | | | |
|---|---|---|---|
| 6,529,446 B1 | 3/2003 | de la Huerga | |
| 7,502,666 B2 * | 3/2009 | Siegel | G16H 20/13 700/244 |
| 7,705,734 B2 * | 4/2010 | Martinelli | G09F 3/0335 340/572.8 |
| 8,242,915 B2 * | 8/2012 | Yan | B65D 41/485 340/572.8 |
| 8,319,613 B2 * | 11/2012 | Lazar | A61J 7/0481 340/309.16 |

(Continued)

OTHER PUBLICATIONS

Bennadi D. (2013). Self-medication: A current challenge. Journal of Basic and Clinical Pharmacy, 5(1), 19-23.

(Continued)

*Primary Examiner* — Michael Collins
(74) *Attorney, Agent, or Firm* — Anton J. Hopen; Smith & Hopen, P. A.

(57) ABSTRACT

Ingestible product and medical device containers validate self-administration of the product and/or corresponding use of the device over a schedule. A machine-readable optical code label such as a QR Code is affixed to an interior surface of a container containing the product or device. The container must be open to electronically read the optical code label. The label contains data associated with the product or device is read by a software application installed on a smartphone. The software receives the label-embedded data and a timestamp to validate the patient is self-administering the medication or device consistent with a schedule.

7 Claims, 19 Drawing Sheets

(56) References Cited

U.S. PATENT DOCUMENTS

| | | | |
|---|---|---|---|
| 9,345,645 B1* | 5/2016 | Chernyak | A61J 7/049 |
| 9,367,849 B1* | 6/2016 | Smith | G01J 1/02 |
| 10,825,559 B1* | 11/2020 | Hopen | G16H 80/00 |
| 11,017,893 B2* | 5/2021 | Hopen | G16H 20/10 |
| 2005/0127155 A1* | 6/2005 | Claessens | G06K 19/07758 |
| | | | 235/375 |
| 2006/0231109 A1* | 10/2006 | Howell | A61J 7/0076 |
| | | | 128/898 |
| 2007/0050083 A1* | 3/2007 | Signorelli | G07F 9/026 |
| | | | 700/241 |
| 2008/0027291 A1 | 1/2008 | Williams-Hartman | |
| 2009/0138122 A1* | 5/2009 | Wagner | A61G 12/001 |
| | | | 700/226 |
| 2010/0270257 A1* | 10/2010 | Wachman | G06Q 10/10 |
| | | | 215/228 |
| 2014/0188502 A1* | 7/2014 | Defrank | G16H 40/67 |
| | | | 705/2 |
| 2015/0027918 A1* | 1/2015 | Chaturvedi | A61J 7/04 |
| | | | 206/459.1 |
| 2016/0120759 A1* | 5/2016 | Chen | A61J 7/0481 |
| | | | 340/573.1 |
| 2020/0160756 A1* | 5/2020 | Gantt | G09F 3/02 |
| 2020/0188233 A1* | 6/2020 | Taylor | A61J 7/0409 |
| 2021/0157894 A1* | 5/2021 | Yamagishi | G06T 7/00 |

OTHER PUBLICATIONS

Michael, C. A., Dominey-Howes, D., & Labbate, M. (2014). The antimicrobial resistance crisis: causes, consequences, and management. Frontiers in Public Dealth, 2, 145.

Rather, I. A., Kim, B. C., Bajpai, V. K., & Park, Y. H. (2017). Self-medication and antibiotic resistance: Crisis, current challenges, and prevention. Saudi Journal of Biological Sciences, 24(4), 808-812.

* cited by examiner

🏠 🔒 nscan.azurewebsites.net ⑨ ⋮

GuardianMT ☰

Scan | Home | Schedules

Schedule Medication

Enter in your prescription details.

160 — Vitamin C ▼
What medication are you scheduling? (add new)

170 — 1 ▼
How many pills/capsules do you take at a time?

180 — Once a Day ▼
How many times per day?

190 — 60
How pills in your bottle total?

200 — Save Schedule and link to QR Code

MEDICATION ADHERENCE METHOD AND APPARATUS

CROSS REFERENCE TO RELATED APPLICATIONS

This application is a continuation-in-part of and claims priority to U.S. Non-Provisional patent application Ser. No. 17/074,927 entitled "Medication Container for Dosage Compliance" filed Oct. 20, 2020, which is a continuation of and claims priority to U.S. Non-Provisional patent application Ser. No. 16/558,746 entitled "Interiorly Positioned Machine-Readable Data Labels for Prescription Compliance", filed on Oct. 3, 2019 (now U.S. Pat. No. 10,825,559 issued on Nov. 3, 2020).

BACKGROUND OF THE INVENTION

1. Field of the Invention

This invention relates to consumable and medical device product containers and methods to improve patient adherence with a scheduled regiment.

2. Brief Description of the Related Art

What is needed in the art is a simple, inexpensive way to validate and monitor a patient's compliance to a dosage schedule and full completion of a course of prescribed medication or product.

Lack of adherence to scheduled dosage of prescribed medicine has significant detrimental consequences to both individual patients and public health. Lack of compliance to antibiotic treatment courses and improper self-medication are key contributors to the increase in drug-induced diseases and the development of antibiotic resistance. Bennadi D. (2013). *Self-medication: A current challenge.* Journal of Basic and Clinical Pharmacy, 5(1), 19-23. doi:10.4103/0976-0105.128253. Self-medication is the most common reason for the development of human pathogen resistance to antibiotic drugs. Michael, C. A., Dominey-Howes, D., & Labbate, M. (2014). *The antimicrobial resistance crisis: causes, consequences, and management.* Frontiers in Public Health, 2, 145. doi:10.3389/fpubh.2014.00145. The general public's involvement as an active contributor to antibiotic resistance crisis needs to be solved through proper awareness initiatives. Rather, I. A., Kim, B. C., Bajpai, V. K., & Park, Y. H. (2017). *Self-medication and antibiotic resistance: Crisis, current challenges, and prevention.* Saudi Journal of Biological Sciences, 24(4), 808-812. doi:10.1016/j.sjbs.2017.01.004

Increasing adherence with self-medication has several advantages including effective treatment of illnesses and lower rates of re-admission. Long-term benefits include, but are not limited to, extending autonomy for patients, establishing electronic records of recently taken medications for emergency personnel and early warning for potential drug interactions.

According to the CDC, between 2015 and 2018, 48.6% of Americans have used at least one prescription drug in the past 30 days and 24% of Americans have used three or more prescription drugs. Centers for Disease Control and Prevention. (2021, Mar. 1). *FastStats—Therapeutic Drug Use.* Centers for Disease Control and Prevention. This does not include the number of Americans taking over the counter drugs or those prescribed medications that they have not taken.

In a 2018 article, Watanabe and colleagues estimated that the annual cost of prescription drug-related morbidity and mortality due to non-optimized medication therapy was $528.4 billion in 2016 US dollars. The plausible estimated range was between $495.3 billion to $672.7 billion. Medication optimization when applied means continually adjusting medication treatments to allow them to reach their full benefit in improving patient outcomes. Practically this may include dosage adjustment, changing medications, detection of interactions, management of side effects, patient education and especially medication adherence. To effectively optimize medications, there must be of continual review and adjustment of medication therapy and adherence to the determined treatment plan. Additionally, adherence data is necessary to accurately identify and correct potential problems, ex: it is discovered that a patient is non-adherent to their anti-hypertensive medication. Using this data, the pharmacist decides to counsel their patient rather than suggest transitioning to a second-line medication. Until now, optimizing medications using adherence data on a large scale has not been realistic without spending a massive amount of money on digital medication bottles. The implementation of a low-cost adherence tracking and medication management tool provides the opportunity to offer highly effective medication management therapy to all patients.

Opioid Management Therapy

In the age of the opioid epidemic, prescribers are often conflicted when choosing whether or not to prescribe a narcotic. If they do not prescribe, they risk withholding pain relief from those who need it. Alternatively, if they do prescribe, they risk putting these drugs into the wrong hands and contributing to addiction and overdose. Our system can aid prescribers in this decision process.

For those with chronic pain who wish to utilize opioid treatment, they may be registered into a prescription drug monitoring program (PDMP). Similar to the IPLEDGE program for isotretinoin treatment, patients must adhere to certain standards to stay in the program. All prescribing providers can access data from this program to determine if it is appropriate to prescribe a narcotic to their patient. This can help negate the problem of patients receiving multiple opioids from several different providers and pharmacies without their knowledge.

BRIEF SUMMARY OF THE INVENTION

The present invention is a method and system of validating self-administration of prescription medication by a patient. Specifically, the prescription medication is administrable over a series of timed dosages (for example, taking three capsules per day over 10 days).

An embodiment of the invention includes affixing a machine-readable optical code label on an interior surface of a prescription medication container containing the prescribed medication. Imprinting of the label may be performed onto an adhesive label which is affixed to the interior surface of the prescription medication container. The machine-readable optical code label may include a format that contains sufficient data capacity to be useful. Embodiments of the invention place the optical code label on the interior face of the bottle cap, the interior bottom surface of the bottle and the interior surfaces of the bottle's cylindrical sidewalls. Each placement has certain advantages. For example, placing the label on the cap forgoes any visual occlusion by remaining pills or capsules in the bottle. However, if the patient is taking multiple prescriptions, and opens multiple bottles simultaneously, then the wrong cap may be put back on the wrong bottle. Putting the label on the bottom of the container would typically only be useful for an application that confirms all medicine has been consumed (e.g., an empty bottle). Placing the label on the upper, interior, sidewall surface of the bottle may be advantageous as the label remains associated with the vessel containing the medicine and is independent of caps being interchanged between bottles. It would also be viewable in most circumstances even with substantial amounts of medicine remaining in the bottle. Various types of machine-readable optical labels are still readable even if there is a partial occlusion of the label.

For example, a UPC-A barcode may contain an integer associated with a primary key that, in turn, links to a specific prescription. However, a two-dimensional matrix may contain far more information including the alphanumeric data specific to the prescription including the patient name, prescribing provider, prescription date, dosage instructions, side-effect warnings and the like. Matrix labels may include those as AZTEC CODE (International Standard: ISO/IEC 24778), DATA MATRIX (International Standard: ISO/IEC 16022), DOTCODE (Standardized as AIM Dotcode Rev 3.0.), MAXICODE, QR CODE (International Standard: ISO/IEC 18004), and the like. For the purpose of this disclosure, a terse prescription may be conveyed in 50 characters which would require a 33×33 QR Code. However, for most embodiments of the invention to convey full prescription data without requiring a round-trip to an external server, a QR Code Version 10 (57×57) conveying 174 characters with error-correction using the Reed-Solomon error correction algorithm should be sufficient.

An embodiment of the invention organizes the prescription information into structured data fields so that string and numeric values have context. This permits the software application on a mobile device to scan the optical label and interpret the structured data to organize a dosage schedule within the software application on the mobile device. An advantage of this approach is that the software application does not need access to third party network resources (such as RESTful APIs or web services) to function. By obviating the necessity of these communications, the implementation of this invention is much easier and efficient. Furthermore, sending and retrieving sensitive health information requires additional layers of security and legal compliance. Because all the same information exists in the optical label that exists on the human-readable outside label of the bottle or container, there are no additional security concerns. While mark-up languages liked XML or structured languages like JavaScript Object Notation (JSON) can store data they can be relatively verbose. Accordingly, fixed width and delimited data formats may be used to convey the most characters using less data-dense optical label formats.

Mishandling of prescription medications stems from may circumstances including, but not limited to, forgetfulness, losing the medication, taking the wrong medication out of multiple prescriptions, and willful abandonment of completing the prescribed course of medication. One tenant of the present invention is that proper administration of the medication is far more likely if the patient has the medication in front of them and the container open. One objective of the present invention is to induce and verify that the patient has the medication present and available at the right time consistent with their dosage schedule.

Accordingly, the container must be open to electronically read the optical code label. The optical code label contains the label-embedded data associated with the prescription medication and readable by a software application installed on a portable electronic device such as a smartphone. The software application receives the label-embedded data and a timestamp to validate the patient is self-administering the prescription medication consistent with the series of timed dosages and automatically generates an alert notification to a healthcare administrator responsive to a deviation in the series of timed dosages.

The software application can require various levels of interaction with the patient. On one end of the spectrum, the patient simply initiates the application and points the mobile device in the direction of the optical code label. The software application reads the data from the label and confirms a timestamp from the internal clock of the mobile device. No other interaction is required by the user. Alternatively, embodiments of the invention may show graphic representations of the medication (e.g., pill or capsule) on the screen of the mobile device so that the patient has visual confirmation he or she is consuming the correct medication (the graphic may include the prescribed medication imprint). Data embedded in the label may include telephone or other contact data for the prescribing healthcare provider. Accordingly, the mobile device software, reading the optical label, may automatically generate links and pathways to the healthcare provider without having a separate datastore or configuration process.

For example, the healthcare provider may set aside an email address or web service to receive a message or post message each time the patient scans the label. Since the label already has the patient and healthcare provide information embedded, the process may be automatically handled directly from the mobile device with minimal or no proxy systems in between. Yet another advantage of the present invention is that a "confidential" email or web service URI may be specified in the QR Code but not human-readable. This avoids unnecessary or unintended email or web traffic to designated reception points. For example, an email address may be designed <dosagevalidation444@domain com> which receives structured emails for the patients of the health care provider that confirm they are taking their medications according to this invention.

The location of the label can be placed at one or more locations in the medication container. A typical prescription medication container has a cylindrical body having a closed bottom and an open top and a cap threadably receivable to the open top of the body. The cap is affixed to the open top of the body to secure the medicine inside the container. The cap has an exterior surface facing away from the body when the cap and body are engaged and an interior surface facing the interior of the body when the cap and body are engaged.

In one embodiment of the invention, the optical code label is affixed to the interior surface of the cap. In another embodiment of the invention, the optical code label is affixed to the interior surface of the closed bottom of the cylindrical body. In yet another embodiment of the invention, labels may be placed at both locations wherein the optical code label at the closed bottom of the cylindrical body includes embedded data conveying its position in the prescription medication container whereby scanning of the label is associated with completion of the series of timed dosages because there is no medicine left in the container to occlude the imaging of that label.

The software application installed on the mobile device may read the label-embedded data and generate patient reminders on the mobile device system corresponding with the series of timed dosages.

Global Unique Identifiers (GUIDs)

An embodiment of the invention addresses the efficiency in which containers using the invention may be inventoried and used. This embodiment is applied for electronically tracking ingestible product consumption over a series of timed dosages. A machine-readable optical code encoding a globally unique identifier (GUID) is affixed or imprinted onto the interior surface of a product container cap. The GUID is unique to that individual cap which encloses a container of a product. The optical code is only readable when the container is open, the product accessible, and the interior surface of the cap is scannable. GUIDs are also known as universally unique identifiers (UUID). They are typically 128-bit numbers used to identify data in computer systems. As the name implies, the GUID strings are unique. This does not depend on a centralized authority or cooperation between entities generating them. The probability of a duplicate GUID is not zero. However, it is close enough to zero to be negligible. With randomly generated GUIDs under Request for Comments (RFC) 4122 version 4, the chance of two having the same value can be calculated using the probability theory. The probability to find a duplicate within 103 trillion version 4 GUIDs is one in a billion.

The embodiment of the invention utilizing GUIDs provides an important utility. GUIDs pre-printed on the inside of the container caps: (1) are agnostic as to the medication or product contained; (2) contain no private medical data about the medication or product; and (3) are statistically unique that the risk of a collision between two identical GUID values is negligible. In operation, millions of bottle caps may be imprinted with unique GUIDs by multiple manufacturers without any coordination or central authority provided they are properly randomized under RFC 4122 version 4 or a functional equivalent. When a prescription is filled, the pharmacy may "link" that unique GUID value with the prescription record whereby the patient may scan the GUID value upon each scheduled dose. Alternatively, the patient themselves may initialize the link between the GUID value of container cap and the medication schedule they wish to adhere to.

Scanning GUIDs

Once the GUIDs are imprinted and scannable when the container is open, a schedule of timed dosages for the product is established in a software application operable on a portable, network-connected electronic device. This device is typically a smartphone such as those known under the brands GALAXY, PIXEL or IPHONE. The machine-readable optical code is scanned through a camera in the device to decode the machine-readable optical code back to the GUID. In the next step, a data association is registered between the GUID and the schedule of timed dosages. This is typically done by an update to a GUID field in a table of schedules. The product container GUID and the schedule of medication or product is now linked at the software level. The process is now ready to perform adherence scanning to the schedule. For the very first dose of product, the interior surface of the cap is scanned upon administration of a scheduled dose by the device. Software in the device decodes the GUID from the machine-readable optical code. Both the product administration and schedule of timed dosages are automatically resolved for that product from the prior data association with the GUID. A record of the scheduled dose timestamp is stored whereby the software application updates a database table for the schedule of timed dosages with the timestamp of the last scan of the machine-readable optical code decoded to the GUID. A database query is established that returns records for the schedule of doses when in an overdue state. The database query is polled on an interval to retrieve records for one or more overdue doses. A notification event is fired to alert one or more recipients of the overdue state whereby the one or more recipients are notified to administer the dose of product.

GUID Licensing

An embodiment of the invention provides for licensing of GUIDs for medication adherence monitoring. For example, a manufacturer may decide to imprint 100,000 container cap interior surfaces with unique GUIDs. The GUIDs may be generated at the time of imprinting or pre-generated into a batch list. Each GUID imprinted is then sent (individually or preferably in a batch) to a GUID licensing server and stored in a table including the GUID value, date generated and licensed manufacturer identification. GUID licensing provides flexible revenue models. For example, the manufacture may license the technology wherein they pay $0.05 per container cap imprinted with a unique GUID. Alternatively, the GUID license may invoke a one-time $1.00 charge when a GUID is linked to a prescription schedule. Yet another licensing model may include charging $0.01 per scan of each dose by a licensed GUID value. Upstream in the process, software scanning the GUID make requests to an API server to verify the GUID linked or scanned on a per-dose basis is licensed or rogue. Rogue GUIDs invoke exception handling in the software to handle out-of-license situations. For example, an unauthorized GUID renders use of the software application fully or partially inoperable.

Quantity Tracking

An embodiment of the invention not only tracks adherence but also the quantity of the medication or product left in the container. The method includes initializing a quantity of doses upon the registering of the data association between the GUID and the schedule of timed dosages. For example, there may be 90 tablets of a product initially in a container. The software then decrements the quantity of doses upon each subsequent scan of the interior surface of the cap. Thus, upon the first scan, the quantity of tablets is now 89. The remaining doses are calculated and displayed on the device. The remaining doses may be combined with the dosage interval to extrapolate a date in which the course of medication or product is finished. For medications or products which are ongoing, a threshold value for refilling or reordering additional doses based on the total remaining doses may be set. For example, when less than 10 tablets are left in the container, a refill request is transmitted to a pharmacy or retail store for a resupply.

Reassociation of GUID

A useful feature of the GUID system is the reassociation of a new GUID to an existing schedule of doses. If a user is on an ongoing course of Vitamin C according to the example above, when less than 10 tablets of Vitamin C are left, a new bottle of Vitamin C is delivered. This new bottle has a completely unique GUID. The user then links the schedule of doses with the new bottle's GUID to maintain continuity with the same schedule of dosage and record of adherence.

Over-the-Counter (OTC) Universal Scheduling

Over-the-counter products present an opportunity to minimize user interaction and automate the dosing process. For example, a Vitamin C product sold under the brand AMAZON ELEMENTS VITAMIN C with a UPC label value of 842379103643 has a "suggested use" dosing schedule of "take 1 tablet daily." The product also has a fixed quantity of 300 tablets. For every container with this UPC value, the quantity, product, and recommended schedule is static. In such cases, an embodiment of the invention affixes or imprints onto the interior surface of the product container cap a machine-readable optical code encoding the over-the-counter ingestible product identifier having a universal dosing schedule. The cap encloses the container of the over-the-counter product wherein the optical code is only readable when the container is open, the product is accessible and the interior surface of the cap is scannable.

Unlike the process noted above, there is no need to link or register the optical code with a schedule of doses. The user, pharmacist or healthcare provider need not enter in a dosing schedule because the one provided by the OTC product is universal to all users. Accordingly, there is less required interaction or data entry into the software application on the portable device. The universal dosing schedule may be encoded directly into the machine-readable code, or alternatively, may be retrieved from a remote data store. An advantage of the remote data store is that updates into doses or even product recalls may provide information that otherwise would be inaccessible to the end user. As noted previously, the quantity of the OTC product may be monitored and, in the example herein, a threshold value of 3 remaining tablets may invoke, an automatic AMAZON PRIME 2-day delivery order so the end user achieves "just in time" inventory replenishment of his or her Vitamin C product. In addition to the convenience for the user, the retailer also establishes a greater consumer loyalty and seamless purchase system for continuous reorders.

Multi-User OTC Monitoring

A variant of the OTC product embodiment addresses the situation when multiple users share a container of product. For example, consider if three individuals share the 300-tablet bottle of AMAZON ELEMENTS VITAMIN C. Instead of a 300-day supply, three users (adhering to the universal dosing schedule) will jointly consume the product in 100 days. In such a case, a remote data store records each time one of the plurality of users scans the machine-readable code on the inside of the product container cap. The system then calculates a decrementing quantity of product remaining in the container. Remaining quantities are displayed on the device and also set with threshold to execute automatic reordering of the product.

Blister Packs and Unit Dose Packaging

Unit dose packaging means that one dose of a medication is packaged individually rather than contained together in a bottle, for example. This form of packaging is common in hospitals that incorporate (externally affixed) barcoded medication administration systems. It is also used in common OTC-as-needed medications to allow the consumer to travel with a single dose rather than a bottle.

In this application of the technology, a machine-readable data label is incorporated into this unit dose packaging in such a way that it may only be scanned once the packaging has been opened. Blister packs and UDP have substantial advantages when incorporated with the present invention. It is not financially feasible to apply digital sensors to blister packs and unit dose packaging. While digital bottles and sensors can detect when a medication bottle was opened, QR code utilization produces the same data and similar end results at a fraction of the cost and is not limited exclusively to bottles.

In the UDP and blister pack application, another step in the medication taking process has been proven. In the medication bottle application, the patient must go to their bottle, open it, scan the QR code to mark a dose as taken. In the UDP and blister pack application, the patient still takes the previous steps, but now when they open the container, their exact dose is accessible and cannot be returned to the container. The end result is the patient having their exact prescribed dose on hand and documented.

An embodiment of the invention includes a blister pack for unit-dose packaging. The blister pack has a front surface with a plurality of cavities in which individual doses of product are placed. The doses typically are tablets or capsules. The doses may be a single dose or multiple doses. A rear surface over which a lidding seal encloses the cavities. For each individual dose of product, a front-surface facing machine-readable code associated with the product is imprinted onto or affixed to the lidding seal in alignment with each individual dose of product. In this way, the machine-readable code is occluded until the lidding seal is opened to access the individual dose of product. In an embodiment of the invention, a machine-readable code encodes a common GUID associated with the product contained in all individual doses. For example, a GUID of c8b6ca6c-167b-4636-b534-3e33acbba5e9 is encoded into a QR-code that is displayed opening each lidding seal of each cavity. In another embodiment of the invention, the machine-readable code encodes unique GUIDs for each individual dose. This permits more precise tracking of dosages. This is particularly useful if a bolus is given upon the start of a course of medication. Accordingly, the bolus makes the dosages asymmetrical and a unique GUID for the bolus dose allows patients and providers to track and confirm the correct order of dosing is followed. In yet another embodiment of the invention, an additional identifier is included with the common GUID, the additional identifier associated with each individual dose within the blister packet. The common GUID as a machine-readable code may be used only for registration of the medication and/or schedule of dosages before any individual cavity is opened. Then, the common GUID is combined or appended into encoded machine-readable codes associated with each dosage cavity. In a simple example, an incrementing integer may be appended to the common GUID effectively serializing the doses:

| Dose | GUID encoded into QR-Code |
| --- | --- |
| #1 | 4f43b9ff-e922-4247-b56a-e706136353b6-01 |
| #2 | 4f43b9ff-e922-4247-b56a-e706136353b6-02 |
| #3 | 4f43b9ff-e922-4247-b56a-e706136353b6-03 |
| #4 | 4f43b9ff-e922-4247-b56a-e706136353b6-04 |
| #5 | 4f43b9ff-e922-4247-b56a-e706136353b6-05 |
| #6 | 4f43b9ff-e922-4247-b56a-e706136353b6-06 |

In 2019, the FDA considered requiring fixed-quantity blister packaging for certain opioid pain medicines in order to decrease unnecessary exposure to opioids. In a study of patients with rheumatoid arthritis, it was found that screw on caps and blister packs were the easiest to open. Lisberg R B, Higham C, Jayson M I. Problems for rheumatic patients in opening dispensed drug containers. Br J Rheumatol. 1983 May; 22(2):95-8. doi: 10.1093/rheumatology/22.2.95. PMID: 6850197. Because these are considered easy to open for the majority of patients, this packaging may be applied to all opioids. Utilizing the blister pack embodiment, each pill pouch has an associated QR code. In order to document a dose as taken, the patient must scan the interior QR code via the app. This helps them safely space out doses and raise red flags if doses are missing that have not been taken. Additionally, it may be required that opioids be kept in this original packaging to reduce the likelihood of abuse and accidental overdose. In the case of acute illness or surgery, the patient may be required to return unused opioids after a certain time period has passed, preventing them from saving them.

Medical Devices

An embodiment of the invention applies the same invention approach to medication devices such as an orthodontic retainer that is only worn at night. In such an embodiment, a medical device container is provided for electronically tracking medical device use over a schedule of timed deployments. The container includes a body forming the sides of the container, the container having a closed bottom and an open top. A cover encloses the open top of the container to secure the medical device inside the container while the cover is in a closed state and the cover is movable (e.g., pivotally hinged) to provide exterior access to the medical device while the cover is in an open state. The cover has an exterior surface facing away from the body and an interior surface facing the interior of the body while the cover is in a closed state. A machine-readable optical code label is imprinted or affixed to the interior surface of the cover, the machine-readable optical code encoding data to schedule a series of timed deployments of the medical device. The machine-readable optical code data is retrievable by a smartphone software application installed on a smartphone, wherein the optical code label is only electronically readable by the smartphone when the cover is in an open state.

QR codes part of the monitoring program can have the numeric code underneath for manual entry if a patient does not have access to a smartphone camera. This will allow them to enter in the information even from a computer.

BRIEF DESCRIPTION OF THE DRAWINGS

For a fuller understanding of the invention, reference should be made to the following detailed description, taken in connection with the accompanying drawings, in which:

FIG. 5 is a mobile device UI adding a new medication dosage schedule.

DETAILED DESCRIPTION OF THE PREFERRED EMBODIMENT

Figure 1:
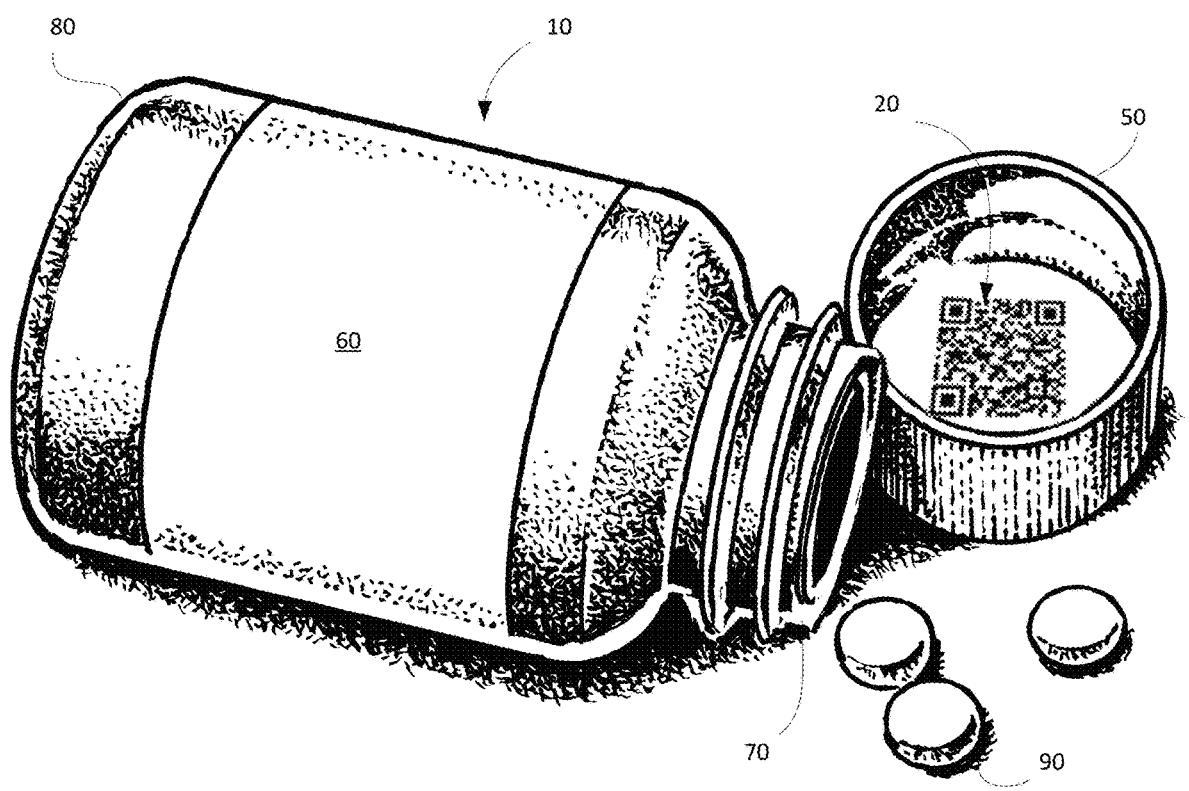
FIG. 1 is an elevated, perspective view of the general application of the invention showing a machine-readable code imprinted to the inside of a medication container cap.

Turning now to FIG. 1, a medication container 10 has bottom 80, outer label 60, mouth 70 and cap 50. Cap has an interior surface upon which a machine-readable code 20 is affixed and is otherwise occluded from view when cap 50 is secured to mouth 70. The term medication is intended to include supplements, vitamins, over-the-counter medication, and prescribed medications that are scheduled over a plurality of doses. In FIG. 1, medication 90 is shown as tablets but other forms such as capsules, gummies and the like are equally functional. As disclosed in U.S. Pat. No. 10,825,559 from which this application ultimately claims priority and whose specification is incorporated herein by reference, decoding machine-readable code requires the user to remove cap 50 from container 10. Hence, when the machine-readable code is processed by a smartphone application, the contents of bottle 10 are accessible to the patient. This improves medication adherence and optimization over the prior art by establishing inherent accessibility to the medication.

Figure 2:
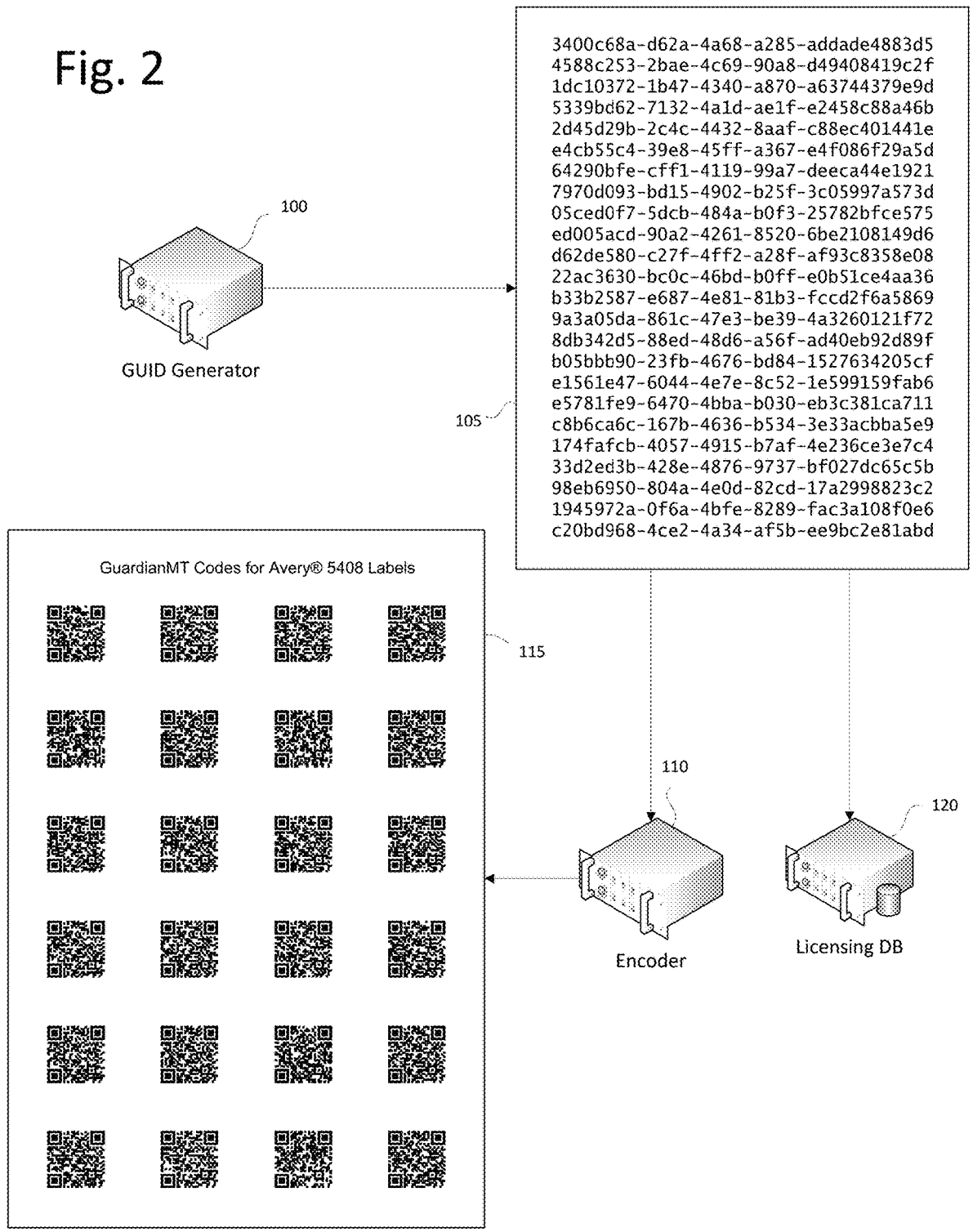
FIG. 2 is a diagrammatic view of an embodiment of the invention generating unique identification codes for individual cap labels.

FIG. 2 shows an embodiment of the invention directed at high-volume deployment of containers using the interior-affixed machine-readable codes. A globally unique identifier (GUID) is a 128-bit number used to identify data in computer systems. When generated according to standards, GUIDs are, for most practical purposes, entirely unique. Their uniqueness does not rely on a central registration authority or cooperation between multiple parties creating them, unlike most other numbering schemes. While the probability that a GUID will be duplicated is not zero, it is close enough to zero to be negligible. A widely accepted standard for GUIDs is the Internet Engineering Task Force (IETF) Standards-Track RFC 4122. In its canonical string representation, the 16 octets of a GUID are represented as 32 hexadecimal (base-16) digits. These are displayed in five groups separated by four hyphens, for a total of 36 characters (32 hexadecimal characters and 4 hyphens). Turning back to FIG. 2, a GUID generator 100 produces GUID array 105 of twenty-four (24) GUID strings. These are sent to a QR-code encoder 110 which produces a 4×6 grid of unique QR-codes on $¾^{th}$ inch AVERY-brand 5408-format circular labels. These labels may be affixed to the interior of container cap 50. When GUIDs are deployed, an embodiment of the invention also sends the 36-character strings to licensing database 120. This provides a verification in approved applications that the GUID code is not used for infringing or otherwise rogue purposes.

An advantage of generating unique QR-codes is that no confidential patient or medication information is present. The unique QR-code is completely agnostic as to the medication, supplement, vitamin or any other multi-dose product in the container. The data relating to dosage, schedule and adherence is maintained in or through the software application that reads and decodes the QR-code.

Yet another advantage of generating unique QR-codes is that large inventories of containers may be maintained without concern they must be associated with a particular patient or medication. The use of adhesive labels is only one embodiment. Additional embodiments include high-volume imprinting, etching or the like of the codes through mass-production. A pharmacist need not manually print an individual QR-code label for a prescription. Rather, they pull a pre-printed cap off-the-shelf and simply link the unique identifier to the prescription that is filled. Alternatively, the pharmacist may leave it to the patient to link the prescription to the QR-code upon taking the first dose.

Yet another advantage of the unique QR-codes is transferability. For example, if a patient is traveling, they might only want to travel with a small amount of medication. A smaller container with its own unique QR-code holds the "travel" doses and the user temporarily associates that unique QR-code with the dosage schedule. When the traveler returns home, they reassociate the dosage schedule with the original medication container QR-code for seamless medication adherence.

Figure 3:
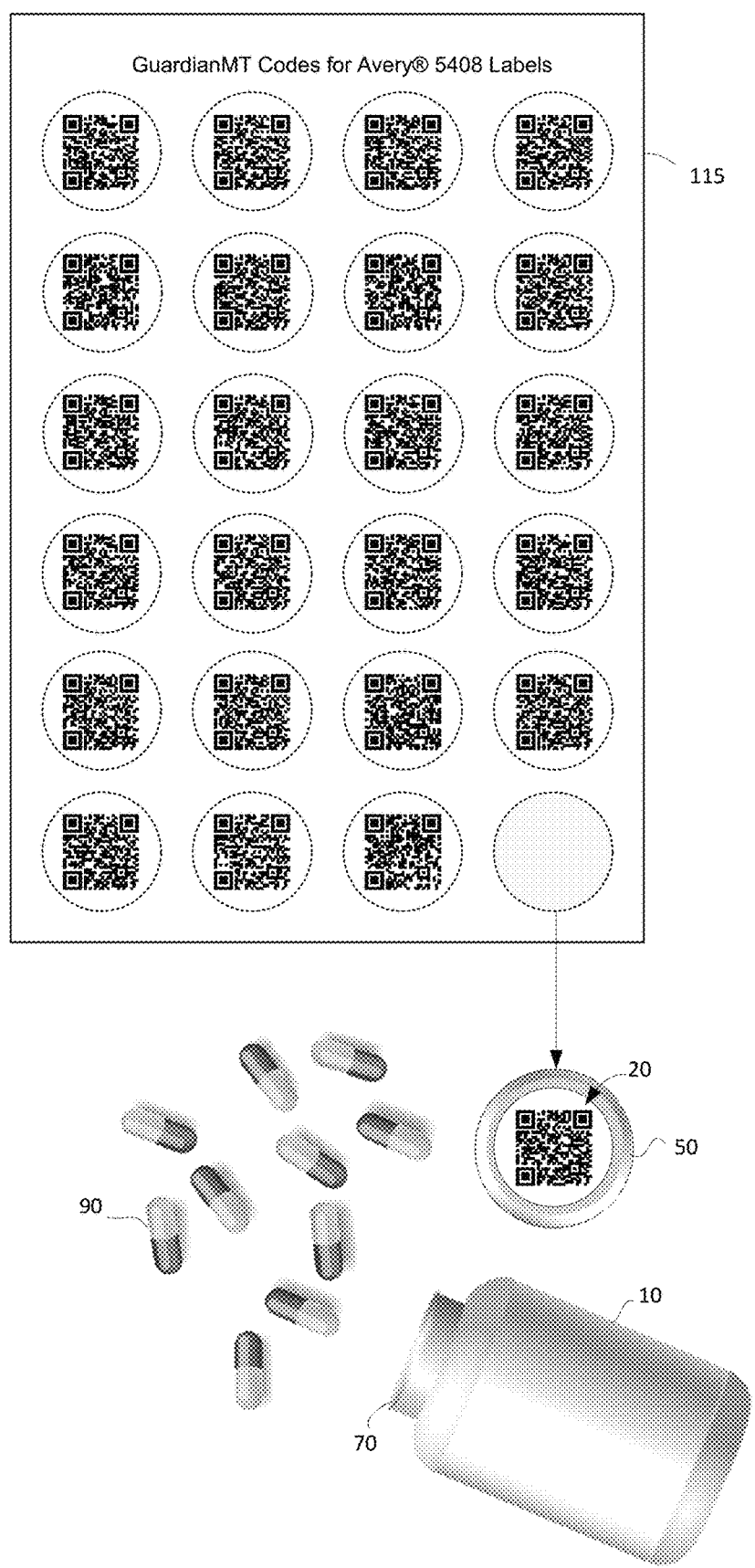
FIG. 3 is a diagrammatic view of an embodiment of the invention showing adhesive labels affixed to the inside of a medication container cap.

FIG. 3 shows the detachment of an individual adhesive label containing a QR-code 20 and affixing it to the interior surface of a container cap 50. All the QR-codes on label sheet 115 are unique GUIDs verifiable through any decoding application.

Figure 4:
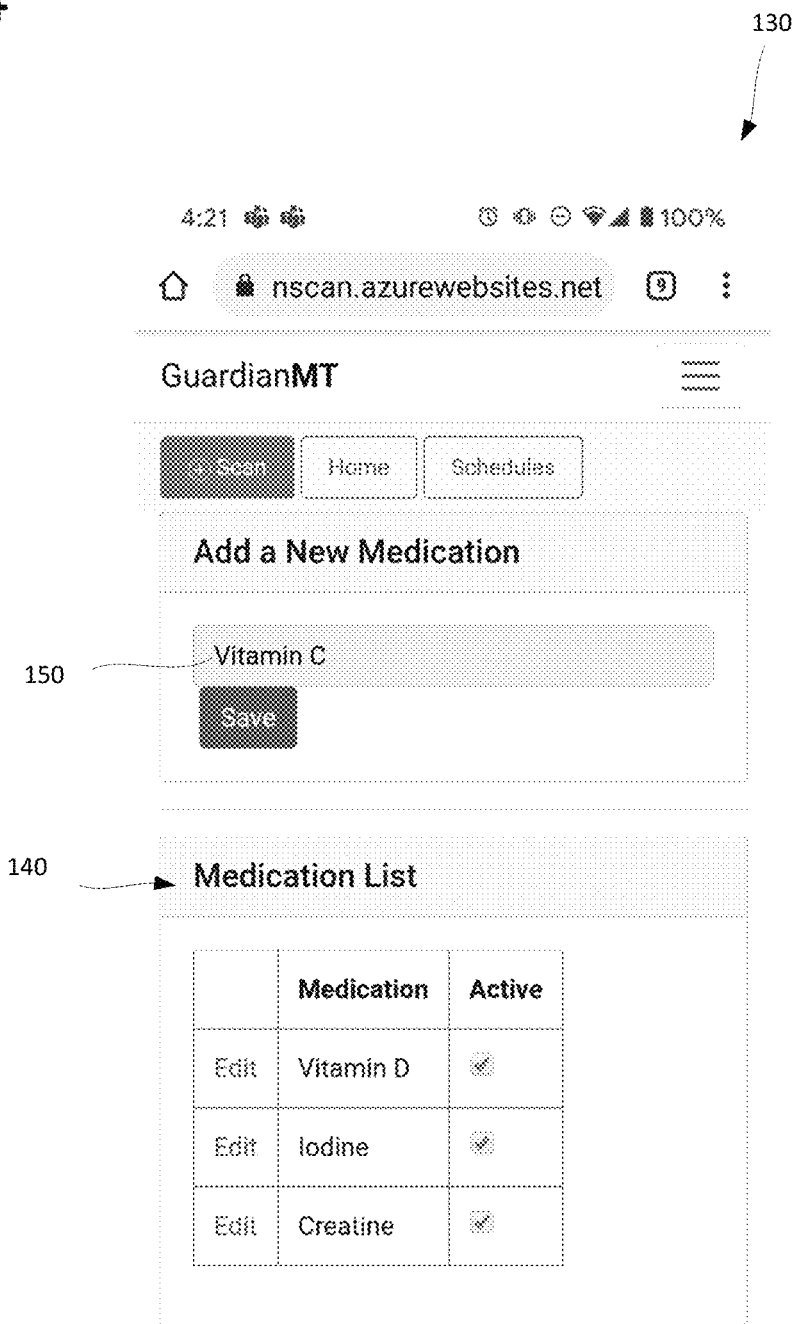
FIG. 4 is a mobile device user interface (UI) adding a new medication for a user.
Figure 6:
FIG. 6 is a mobile device UI scanning a machine-readable code affixed to the interior of a medication bottle cap to link the code with a dosage schedule.

FIGS. 4-10 demonstrate an embodiment of the invention through a smartphone UI. In FIG. 4, UI 130 receives a new medication string value 150 which it adds to medication list 140. In the example, the string value is "Vitamin C" The string 150 is inserted into a medications table which returns the primary key of the inserted row returned by SCOPE_IDENTITY( ) from MICROSOFT SQL SERVER. In FIG. 5, the primary key is used to select the just-inserted string in dropdown list 160. FIG. 5 accepts data to schedule dosages. This includes the quantity of units per each dose 170 (e.g., 1 or 2 tablets); the frequency 180 (e.g., "Once a Day"); and the total quantity of units 190 (e.g., 60 pills). A "save" control 200 sends the data to a database and returns get another SCOPE_IDENTITY( ) value for the primary key for the just-inserted row in a schedule table. This primary key is then passed onto a scan function shown in FIG. 6.

Figure 7:
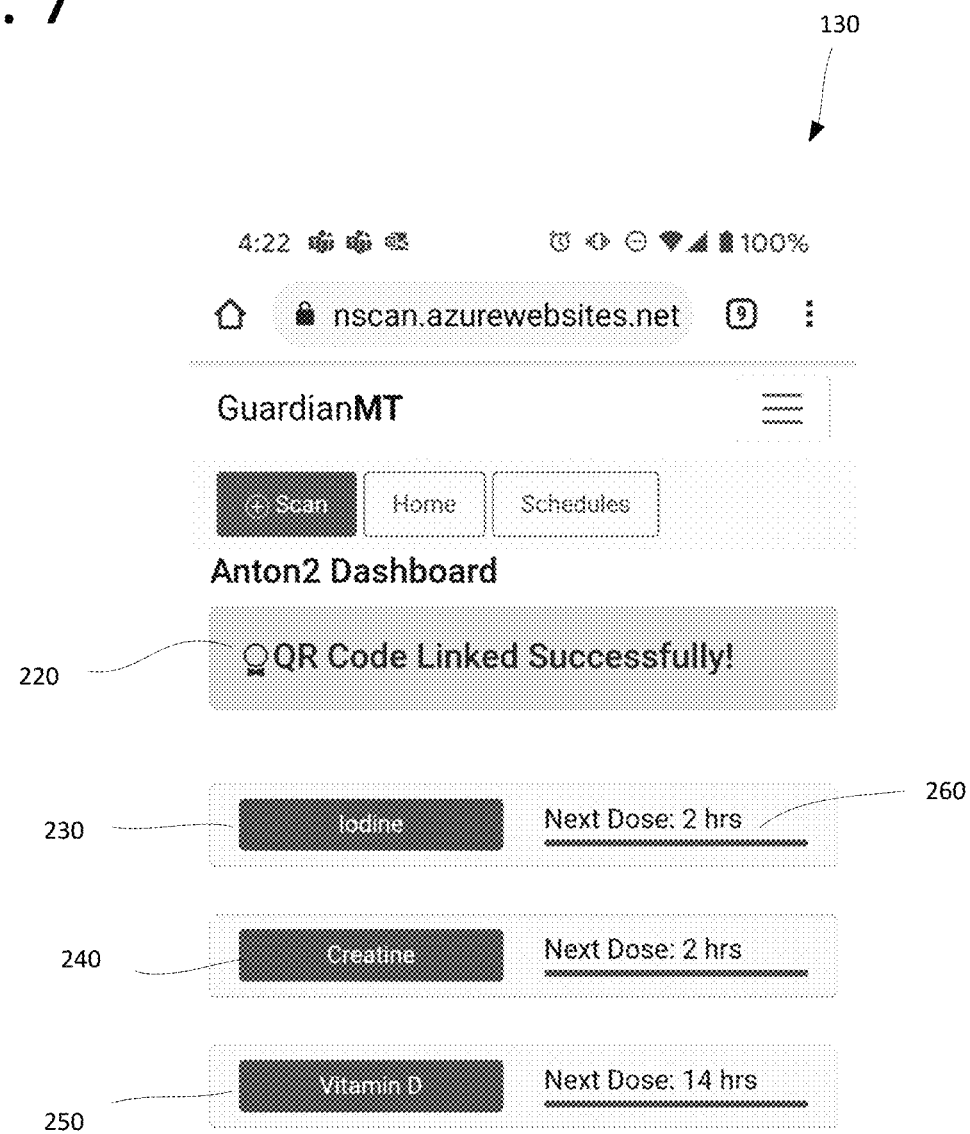
FIG. 7 is a mobile device UI showing confirmation that a machine-readable code identifier is linked to a dosage schedule.
Figure 8:
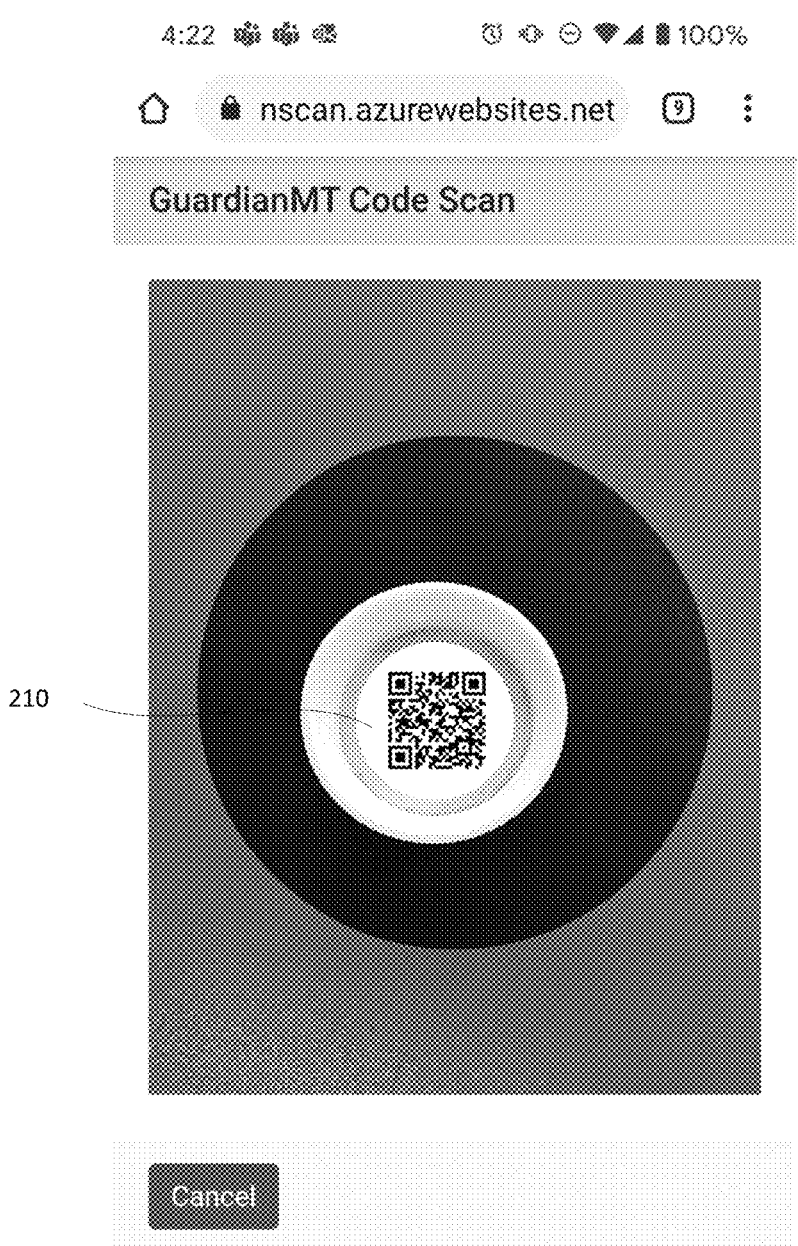
FIG. 8 is a mobile device UI showing the scanning of a machine-readable code affixed to the interior of a medication bottle cap representing the administration of a dose.
Figure 9:
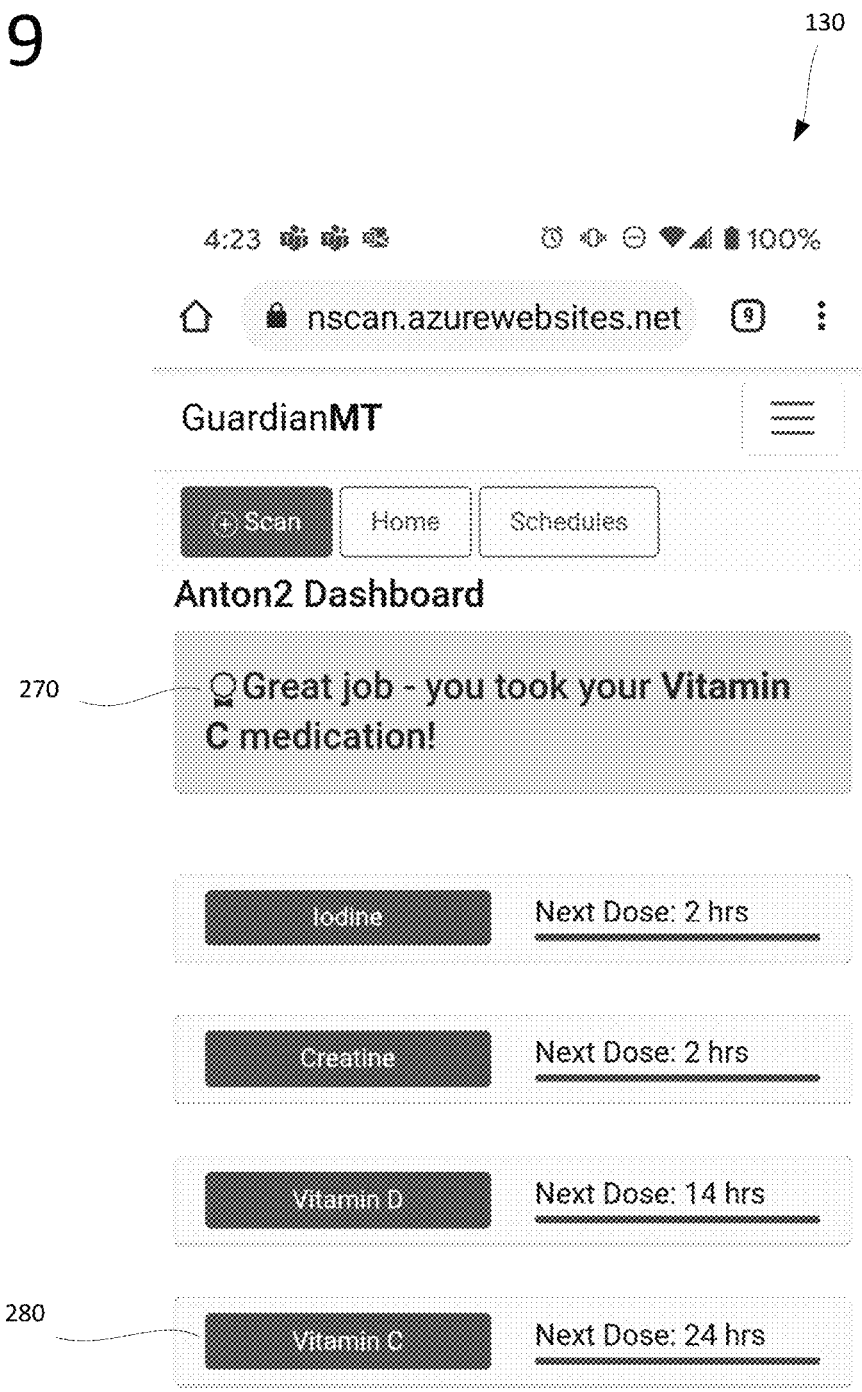
FIG. 9 is a mobile device UI showing confirmation that a machine-readable code identifier was decoded and the dosage schedule updated to reflect the consumption of a dose.
Figure 10:
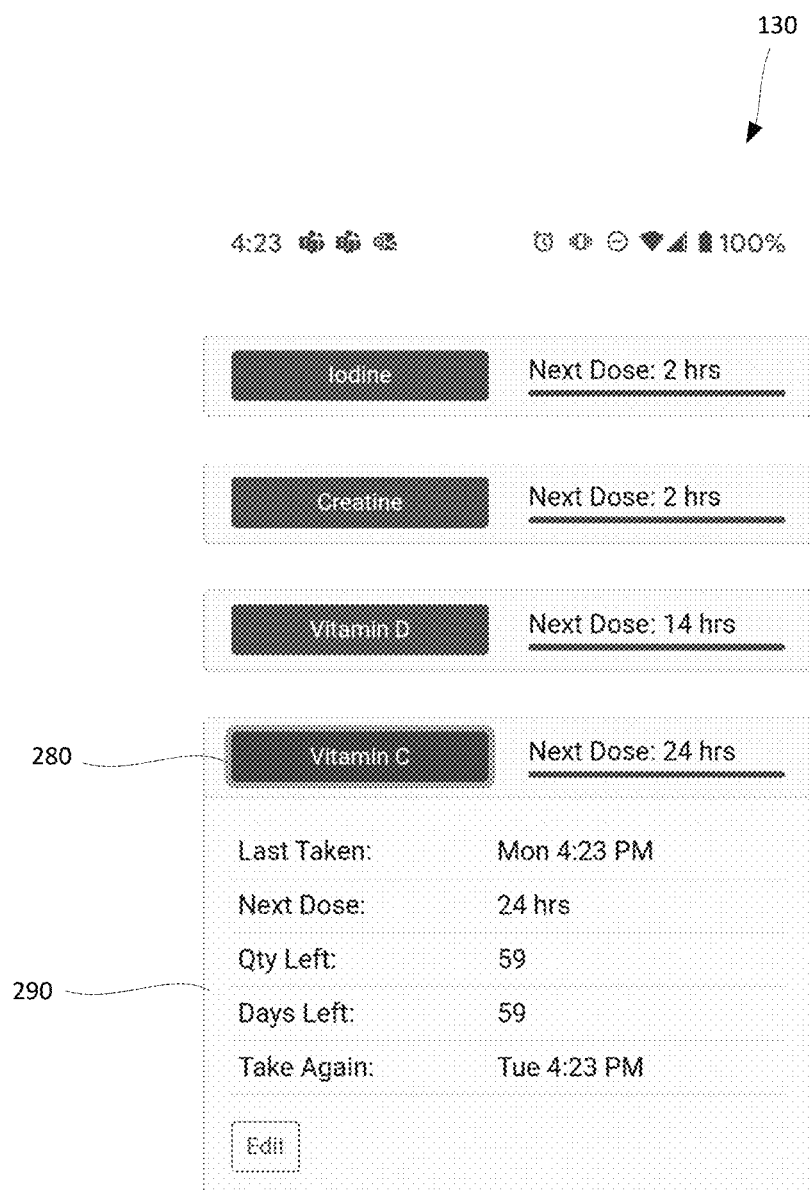
FIG. 10 is a mobile device UI showing expanded details of a dosage schedule in-progress.

Scanning window 210 opens rear-facing camera on the device for the registration process. To help position the camera, a partially opaque window is overlaid on window 210 to help center the camera to the interior face of container cap 50 displaying the QR-code. The registration process in FIG. 6 links the decoded QR-code with the schedule for dosages. This is only necessary once. In FIG. 7, a confirmation 220 is displayed showing the QR-code was linked successfully to the schedule of dosages. Existing schedules for Iodine 230, Creatine 240 and Vitamin D 250 are displayed with countdown values 260 to the next scheduled dose. When the QR-code now linked with the Vitamin C schedule is scanned against in FIG. 8, a confirmation is shown in FIG. 9 that the dose was recorded. The Vitamin C schedule 280 is now shown in the list of schedules and the next dose is noted to be taken in 24 hours (e.g., once-a-day). The button 280 for the Vitamin C schedule activates an accordion control in FIG. 10 to display additional details 290. It should be noted that each time the associated QR-code for the Vitamin C container is scanned, the total quantity left is decremented by one (e.g., 60−1=59).

Figure 11:
FIG. 11 is a diagrammatic view of a database schema according to an embodiment of the invention.

FIG. 11 shows a database schema according to an embodiment of the invention. Using MICROSOFT IDENTITY SERVICES, a user table 300 stores the application users. Medication table 310 links users to medications. Medications are incorporated into scripts table 320 which stores dosage schedules. When QR-codes are processed, the data is updated in medLog table 330. SQL queries are polled for dosage reminders which are transmitted by text messaging, email and/or push notifications to the mobile application.

Figure 12:
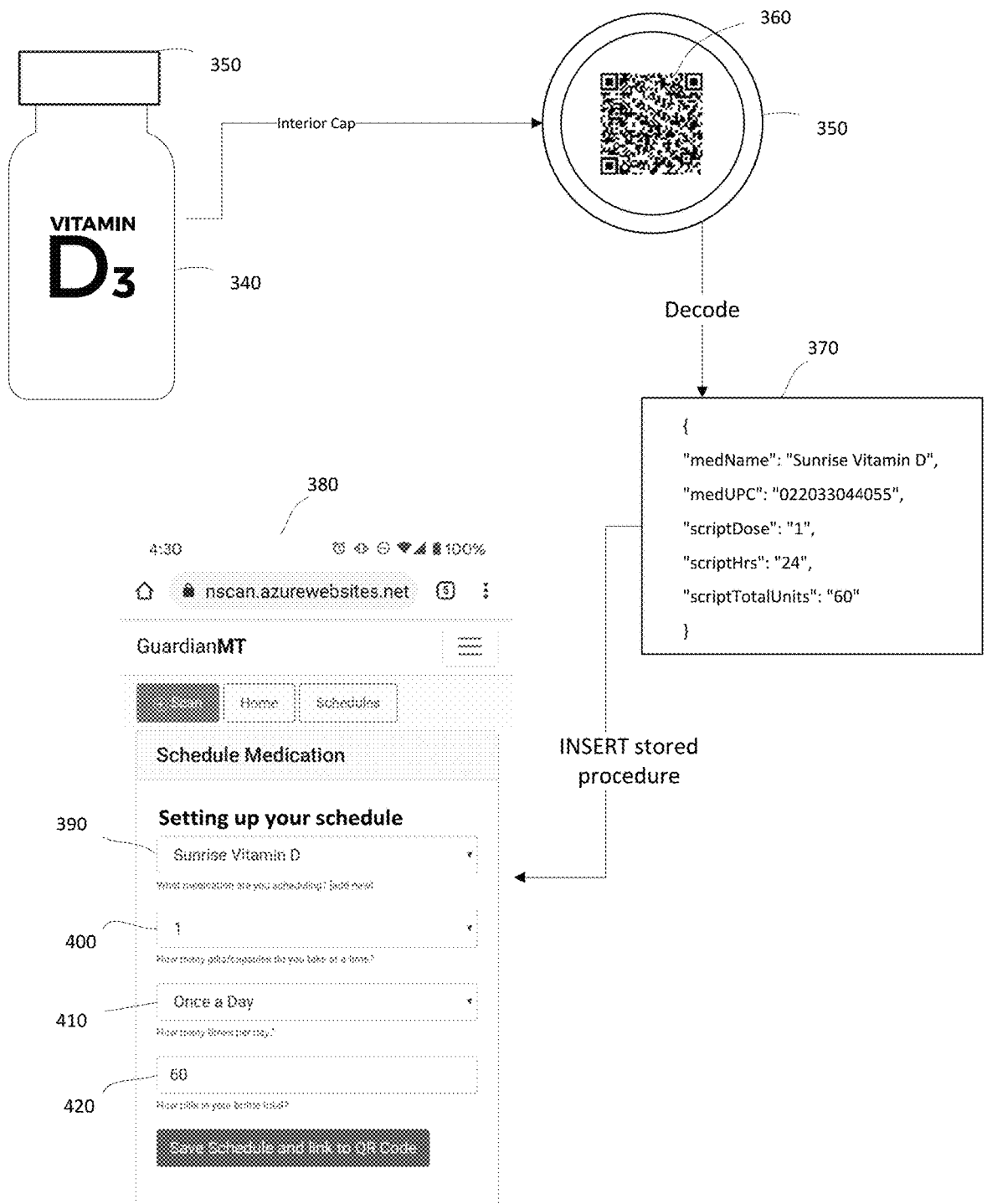
FIG. 12 is a diagrammatic view of an embodiment of the invention for over-the-counter products.

FIG. 12 shows an embodiment of the invention for OTC products. Container 340 for Vitamin D3 is secured by cap 350. Interior surface of cap 350 includes QR-code 360 holding a JavaScript Object Notation (JSON) formatted string 370 containing dosage information for the Vitamin D3 product. This includes its brand-name, universal product code (UPC), dose amount, dose frequency and the total units contained in container 340. This JSON is decoded and the values assigned as parameters in a SQL stored procedure to insert the schedule and medication automatically as shown in UI 380 wherein the brand name is populated as the medication 290, the dose amount in field 400, the frequency in field 410 and the total unit quantity in field 420.

Figure 13:
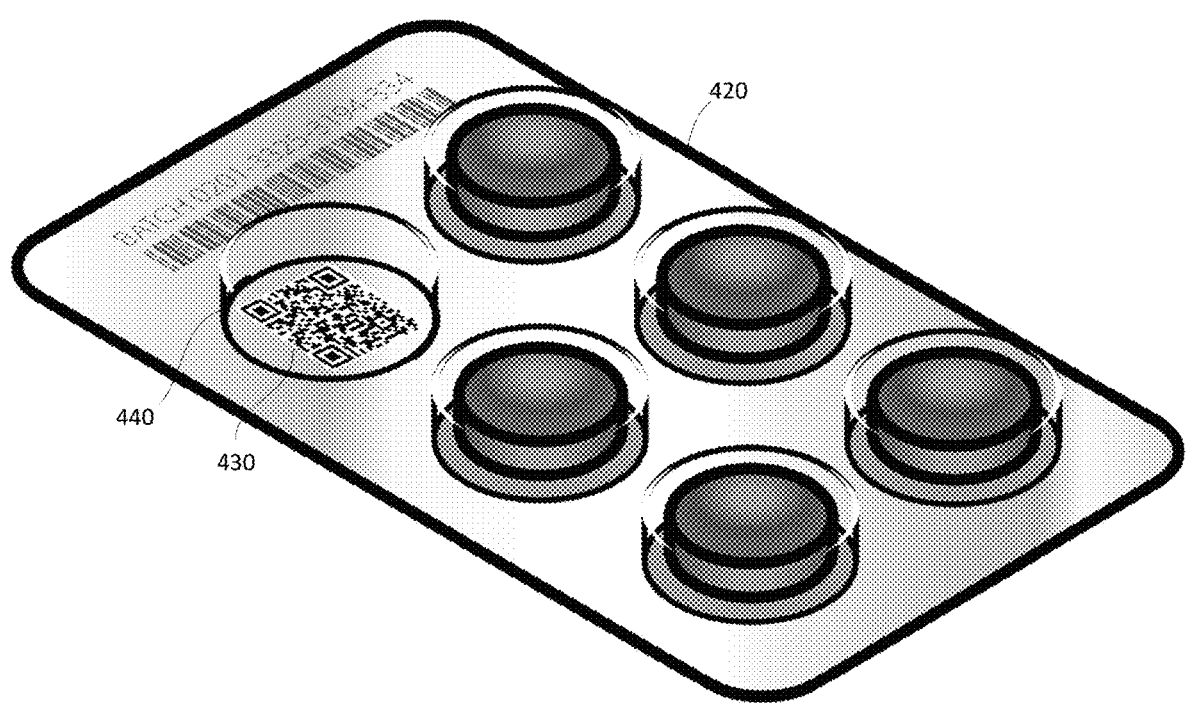
FIG. 13 is an elevated, isometric view of a blister pack medication container according to an embodiment of the invention.

FIG. 13 shows an embodiment of the invention showing a blister pack container 420 having compartments 440 for six tablets. In the embodiment shown QR-code 430 is visible when the tablet is removed. In most blister packs, the tablet is punched through a back foil seal. In such circumstances, the boundaries of the QR-code are reinforced to avoid tearing and damaging the scan integrity of the QR-code graphic. An alternative embodiment is accessing the tablet from the clear encasing through the front of the blister pack so the back foil seal is never broken. In all embodiments, the medication or packaging occludes the scanability of the QR-code while the medication is inaccessible to the patient. However, then the packaging is changed to an open state where one or more doses are accessible to the patient, then the QR-code is scannable and the dose registered in the medication log table.

Figure 14:
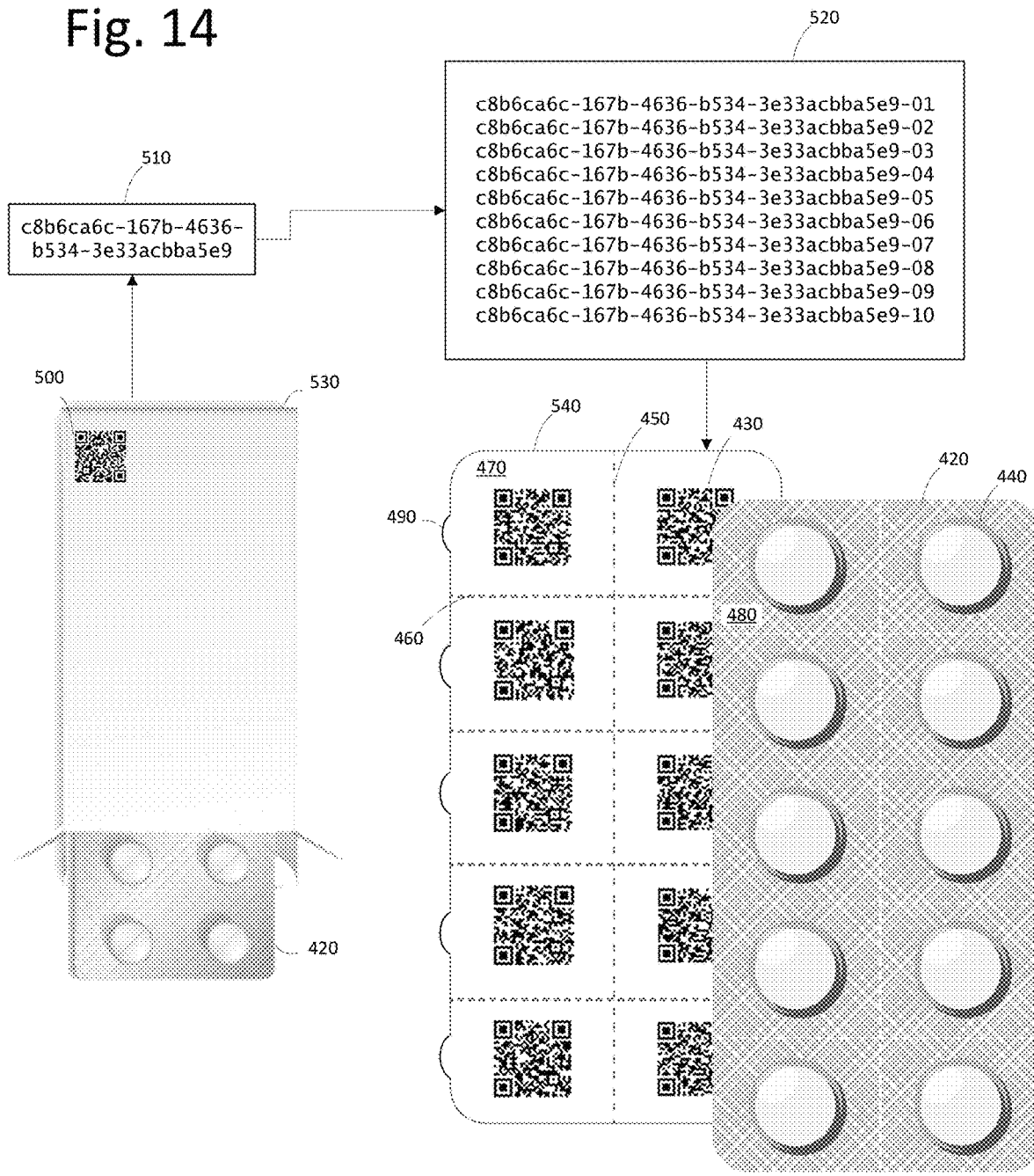
FIG. 14 is a partially diagrammatic view of an embodiment of the invention showing a master code for a blister pack with serialized child codes for each individual dose.

FIG. 14 shows another blister pack embodiment with additional detail. Here, box 530 holds one or more blister packs 420 which, in turn, contain individual doses 440 of medication. It is anticipated by this invention that individual doses may include one or a plurality of units of medication provided they are scheduled similarly. A master GUID 510 is encoded into a QR-code 500 which is registered with the software application according to a schedule of dosing. From the master GUID 510, the individual doses are serialized 520 and appended onto the master GUID 510 value. Each serialized 520 value is associated with each individual dose within the blister pack 420. In the embodiment shown, code backing 540 is affixed to the back of the blister pack 420 wherein the QR-code 430 is occluded from scanning by the presence of medication 440 in its initial state. In this embodiment, tab 490 is pulled away from the back plane of blister pack 420 revealing the QR-code 430 imprinted on a backing segment 470 aligned to dose segment 480. Horizontal perforations 460 and vertical perforations 450 on code backing 540 align with perforations on blister pack 420 so that only the backing segment with the individual QR-code for a single dose is exposed at one time.

Preferably, once scanned, the backing segment 470 of the scanned QR-code is detached and discarded after the associated dose is consumed. The serialization of each individual dose within the master QR-code provides an enhanced level of oversight and adherence as the doses may be inadvertently taken out of order but nevertheless marked as administered by the software application. Furthermore, individual doses may be detached for travel or other purposes but still carry the scannable QR-code specific to that particular dose. Another advantage of this system is in the case of a bolus dose wherein the start of a course of medication may initially call for a higher initial dose. Therefore, the doses in this embodiment may be asymmetrical with the remaining doses but the adherence to the dose schedule is nevertheless maintained.

Figure 15:
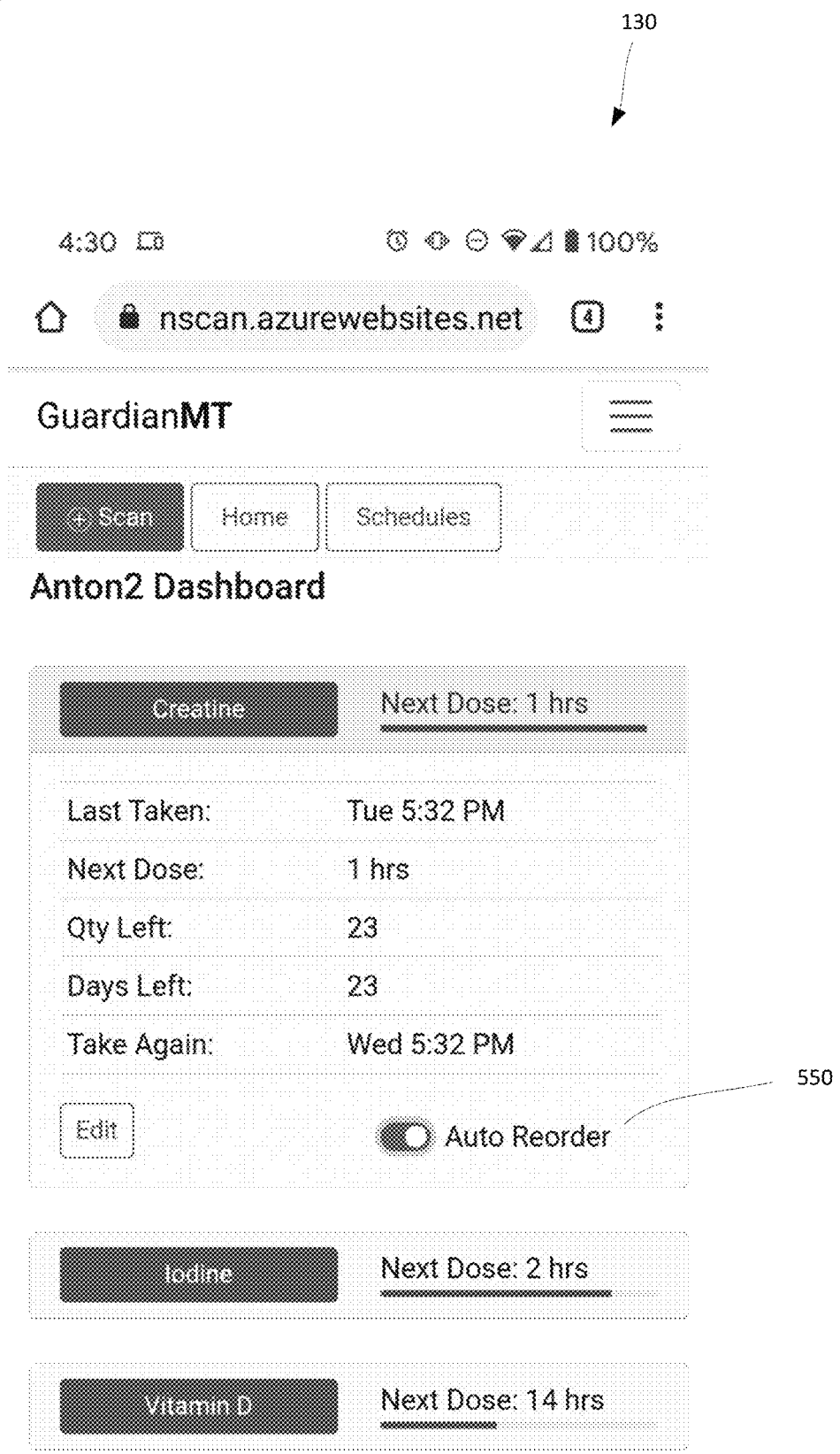
FIG. 15 is a mobile device UI showing an automatic reordering or refilling option when dose quantity falls below a threshold.

FIG. 15 shows an embodiment of the invention having an automatic reordering option 550. For example, for a chronic condition prescription, refills previously were scheduled based on perfect compliance with every scheduled dose. However, under the present invention, the quantity of the remaining doses is decremented upon each scan (e.g., associated administration). Accordingly, refills of prescription medications are automatically implemented only when the patient runs low on the medication. An advantage of this is to reduce the "stockpiling" of unused medication which is dangerous and wasteful. A similar implementation exists for vitamins and supplements such as those sold through AMAZON. If a user wants to maintain adherence to a schedule of Vitamin D3 the application detects when they are low and sends an API request out to AMAZON retailer services to reorder before their current doses are exhausted. This benefits the user in improved adherence to a schedule and improves the experience for the retailer by reducing friction in the reordering process.

Figure 16:
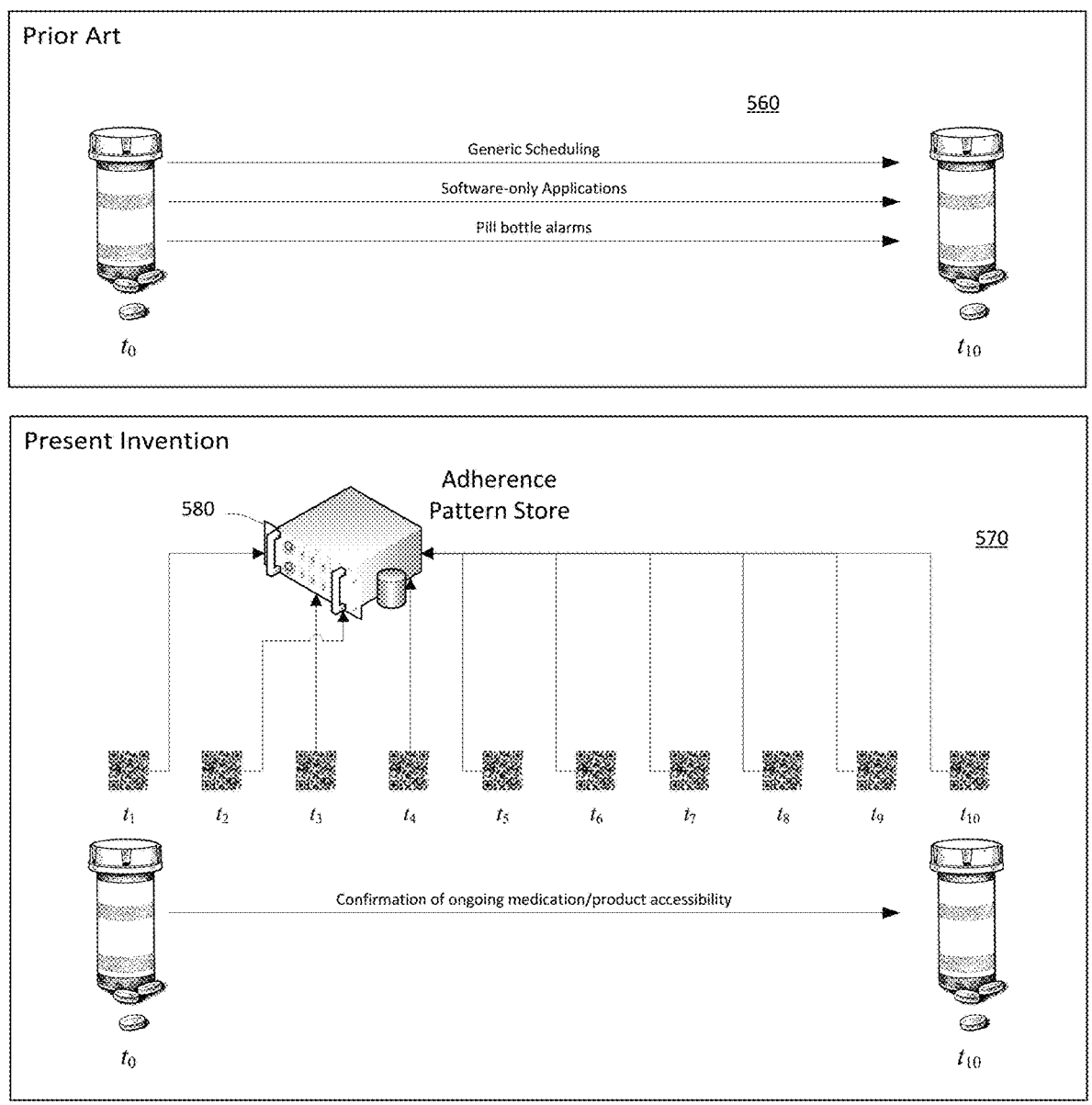
FIG. 16 is a diagrammatic view of the prior art against the present invention that generates an adherence pattern based on container openings.

FIG. 16 shows a comparison of low-cost, prior art technologies 560 which seek to track the progress of dose administration from $t_0$ through $t_{10}$. Cost efficient technologies rely on user reporting of dose administration. For software-based systems such as those running on mobile devices, this consists of a scheduled reminder and subsequent user confirmation that a dose was administered. However, there is nothing to verify the user was even in proximity of the medication upon user confirmation. It is common that users may falsely acknowledge a dose was taken with the good intention of taking it promptly. However, intervening distractions lead to a false confirmation of administration. This results in both non-adherence and inevitable stockpiling of the medication with surplus doses. Scanning a code on the label container can establish that the user was in proximity to the medication but users can "rapid" scan all their medications to feign adherence without taking the medication. Some users might have difficulty opening the medication container but can nevertheless false claim a dose was administered, sometimes out of embarrassment. The present invention 570 can establish an adherence pattern which is recorded and monitored 580. At each timed-dose interval, the code to establish the dose is occluded from scanning by closure of the container. It is only when the container is open and the medication accessible can the code be registered, and the adherence pattern maintained. Medication adherence under the prior art teachings is, by comparison, speculative. The present invention requires the medication be made accessible. For a user to feign a dose administration under the claimed invention, they would have to go to the medication, open the container, scan the interior of the container cap but (while the medication is fully accessible) decline to take the dose.

Figure 17:
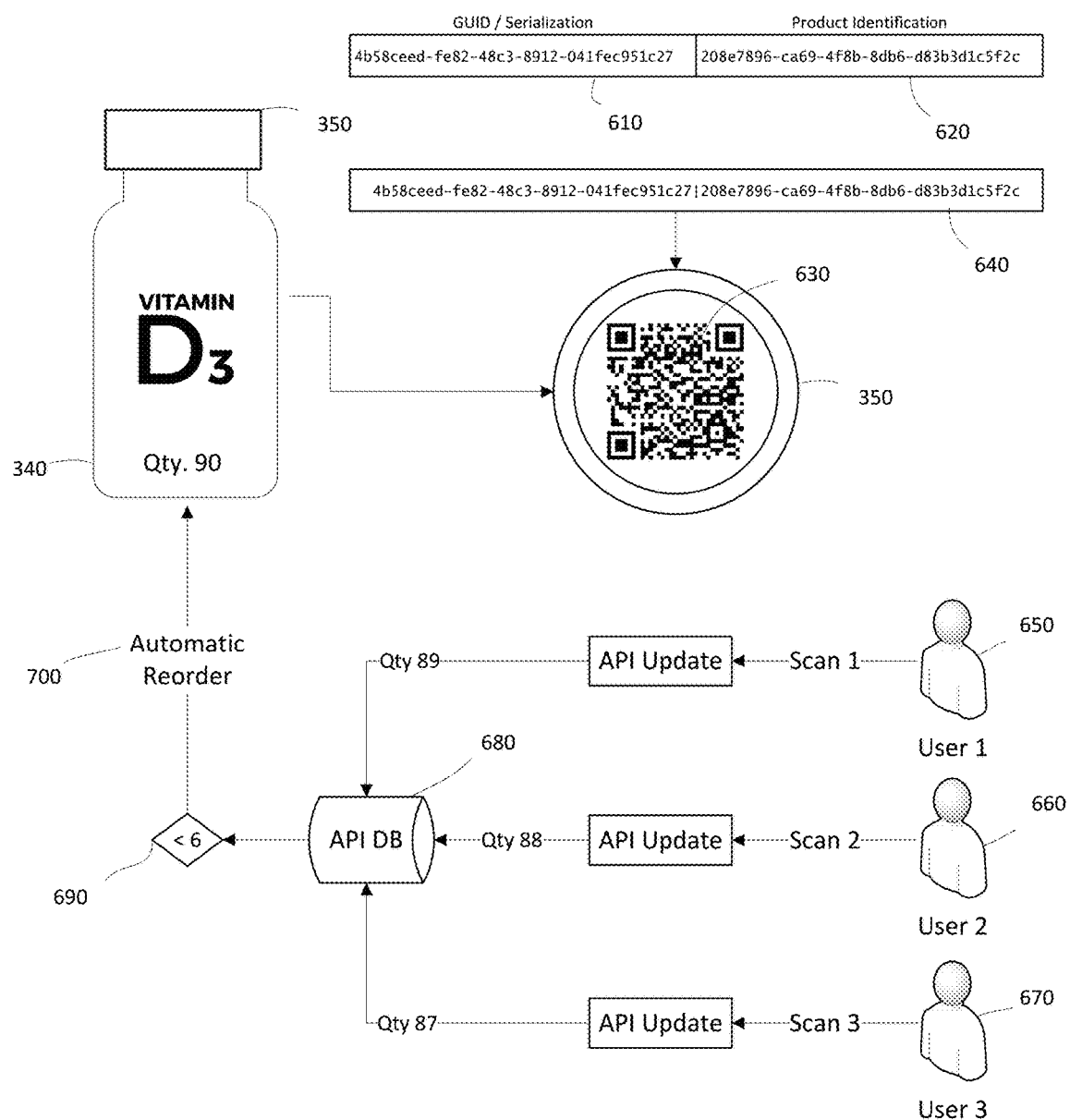
FIG. 17 is a diagrammatic view of an embodiment of the invention showing over-the-counter production consumption tracking in a multi-user environment.

FIG. 17 shows an embodiment of the invention for over-the-counter products that are shared within a household. In this example, a container 340 of Vitamin D3 has a 90-unit quantity. Two string values are appended to generate a combination code 630 on the interior surface of the container cap 350. A first GUID or serialization code 610 is unique to each cap manufactured and labeled. A second product code 620 is associated with retail universal product code (UPC) of the product and the associated directions for use. Users 650, 660 and 670 all share access to the Vitamin D3 product. Upon each dose, the cap is scanned and a master record (stored in API database 680) updates the quantity of the shared container. As shared container remaining quantity reaches a threshold value 690, an automatic reorder 700 event is fired to automatically purchase another container 340. This embodiment of the invention may simply be for inventorying and reordering so the product is continuously available or may also be combined so that adherence to the product is available in a multi-user environment without segregating the product into individual containers.

Figure 18:
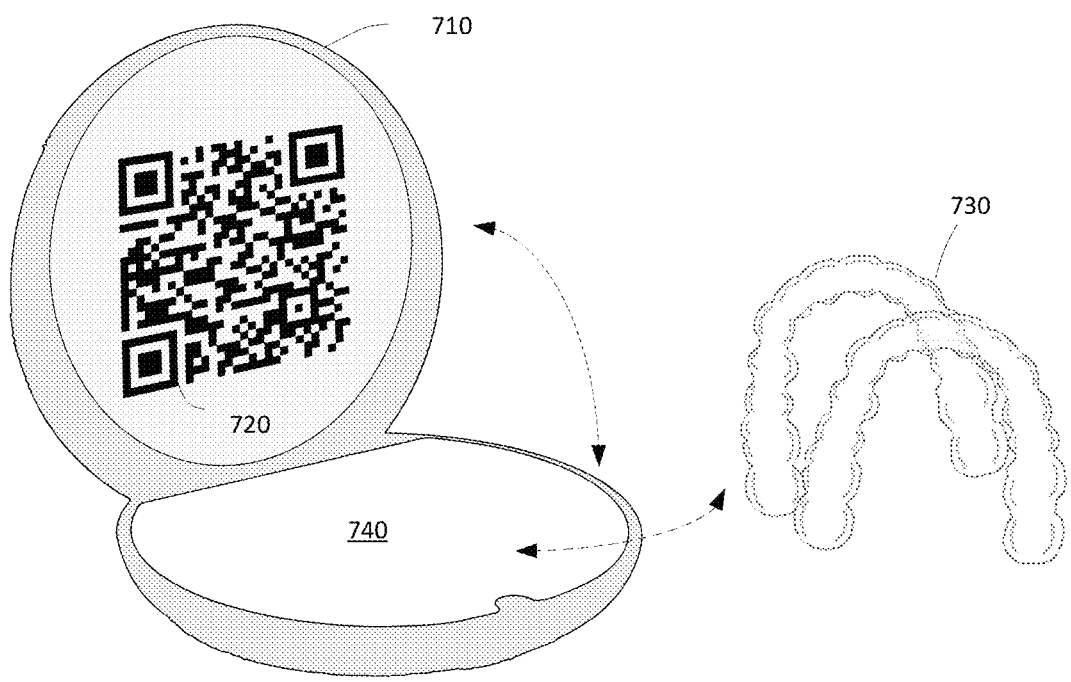
FIG. 18 is a front, elevated isometric view of an orthodontic appliance case embodiment of the invention.

FIG. 18 shows an embodiment of the invention for medical devices that are deployed on a schedule and stored in a container in the interim. In the example shown, orthodontic retainers 730 are stored in retainer case 740 which opens and closes in a clamshell manner. Top portion 710 of retainer case 740, while in an open position, exposes QR-code 720. According to an embodiment of the invention, the retainer case 740 is opened, the QR-code 720 scanned and the retainers 730 deployed overnight. By scanning the QR-code 720 adherence to the nightly use of retainers 730 is monitored and verified. This may be applied to any medical device used according to a schedule and stored in a container that occludes the machine-readable code from scanning while in a closed state.

Figure 19:
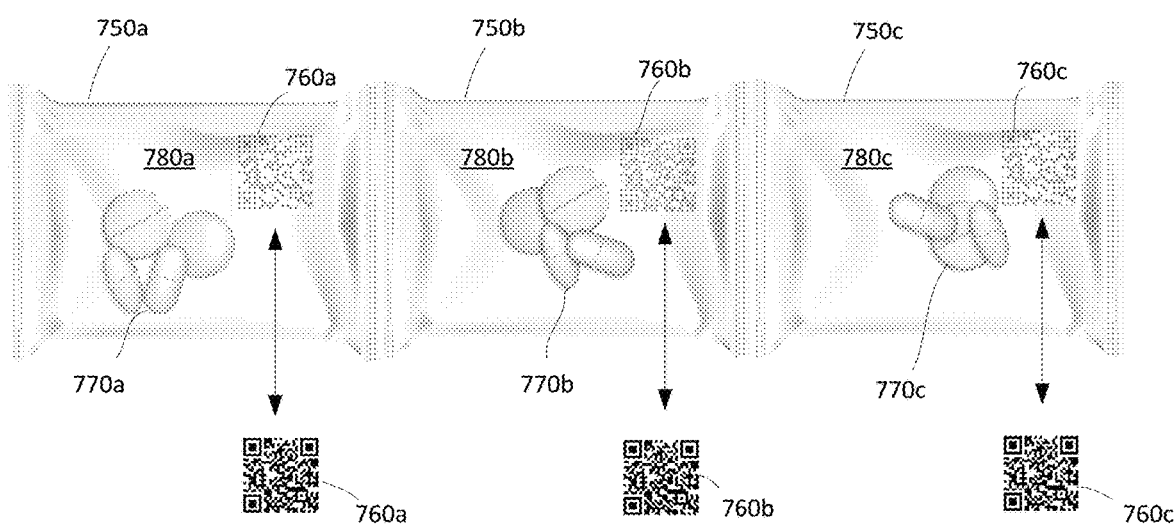
FIG. 19 shows three individual medication pouches connected by a perforated seal having partially occluded scannable QR-codes for dosing adherence confirmation.

FIG. 19 shows an embodiment of the invention for individual medication pouches 750*a-c*. QR-code labels 760*a-c* are affixed into the interior 780*a-c* of each respective pouch wherein the plastic forming pouches 750*a-c* is partially opaque. A patient can see medication 770*a-c* exists in each pouch through the opaque frosting of the plastic but the level of opacity prevents the scanning of interiorly affixed QR-codes 760*a-c* from the exterior of the unopened pouch. Only until each individual pouch is opened to consumer medication 770*a-c* can the QR-code be read by a scanning device. In an alternate embodiment of the invention, QR-codes 760*a-c* are imprinted on in the inside of a bi-fold paper inserted into the interior 780*a-c* of each pouch 750*a-c* wherein the bi-fold must be removed and opened to expose the QR-code for scanning upon each dose.

Glossary of Claim Terms

Administration means the act of consuming a product dosage according to a schedule.

Barcode means a machine-readable optical label that contains information about the item to which it is attached.

Camera means an electronic device component capable of optically scanning a machine-readable code.

Cap means the top enclosure of a container which may be partially or fully removable from the container.

Data association means linking one record to another. For example, updating a column value in a schedule of dosages with a GUID string obtained from decoding a machine-readable code.

Dosage means the rate of application of a quantity of medicine or consumable product.

Globally unique identifier (GUID) means a string of characters randomly generated of sufficient length to be substantially unique without coordination with a central issuing authority.

Licensing Data Store means a database for inserting and querying authorized GUID values allowed to operate with a licensed software application according to the invention.

Medication means a drug used to diagnose, cure, treat, or prevent disease including supplements and vitamins Notification Event means a trigger to send user-detectable output such as a push command to vibrate a smartphone; a push notification to play a sound on a smartphone; a push notification to display a visual alert on a smartphone; a text messaging transmission to a smartphone; an email transmission to a smartphone; and/or an automated voice call to a smartphone.

Optical Code means a representation of data in a visual, machine-readable form.

Patient means a recipient of health care services.

Portable Electronic Device means a mobile device having a screen, camera function and wireless network connectivity.

Prescription (Rx) means a health-care regiment implemented by a physician or other qualified health care practitioner in the form of instructions that govern the plan of care for an individual patient. For this patent specification, the term refers to a course of a prescription drug typically dispensed from a pharmacist.

QR Code (Quick Response Code) is a trademark of Denso Wave Incorporated for a type of matrix barcode. A QR code consists of black squares arranged in a square grid on a white background, which can be read by an imaging device such as a camera and processed using Reed-Solomon error correction until the image can be appropriately interpreted. The required data is then extracted from patterns that are present in both horizontal and vertical components of the image.

Software Application means software running on top of the operating system of a portable electronic device.

Structured Data means any data that resides in a fixed field within a record or file.

Structured data has the advantage of being easily entered, stored, queried and analyzed.

Timestamp means a sequence of characters or encoded information identifying when a certain event occurred, including the date and time of day.

Uniform Resource Identifier (URI) means a string of characters that unambiguously identifies a particular resource, typically on the Internet.

Universal Dosing Schedule means directions provided by over-the-counter products and medications that apply to most consumers of the product.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

What is claimed is:

1. A method for electronically tracking ingestible product consumption over a series of timed dosages, the method comprising:
   affixing, inserting or imprinting onto the interior of a product container a machine-readable optical code encoding an identifier unique to that individual container, the container enclosing an ingestible product wherein the optical code is only readable when the container is open and the product accessible;
   establishing a schedule of timed dosages for the product in a software application operable on a portable, network-connected electronic device;
   decoding the machine-readable optical code through a camera in the device to resolve the machine-readable optical code back to the identifier;
   registering a data association between the identifier and the schedule of timed dosages;
   subsequently, scanning the machine-readable optical code upon administration of a scheduled dose by the device to decode the identifier from the machine-readable optical code;
   automatically resolving both the product administered and schedule of timed dosages for that product from the prior damage association with the identifier;
   storing a record of the scheduled dose timestamp whereby the software application updates a database for the schedule of timed dosages with the timestamp of the last scan of the machine-readable optical code decoded to the identifier;
   establishing a database query that returns records for the schedule of doses when in an overdue state;
   polling the database query to retrieve records for one or more overdue doses; and
   firing a notification event to alert one or more recipients of the overdue state whereby the one or more recipients are notified to administer the dose of product.

2. The method of claim 1 wherein the value of the identifier is stored in a licensing data store.

3. The method of claim 1 further comprising the steps of storing the identifier in a licensing data store and authorizing, through the software application, only a licensed identifier for the data association whereby an unauthorized identifier renders use of the software application fully or partially inoperable.

4. The method of claim 1 further comprising the steps of:
   initializing a quantity of doses upon the registering of the data association between the identifier and the schedule of timed dosages;
   decrementing the quantity of doses upon each subsequent scan of the machine-readable optical code;
   calculating the total remaining doses; and
   displaying on the device the total remaining doses.

5. The method of claim 4 further comprising the step of calculating the remaining time left on the schedule of timed dosages based on the total remaining doses and displaying on the device the total remaining time left taking the product according to the schedule of timed dosages.

6. The method of claim 4 further comprising the step of setting a threshold for refilling or reordering additional doses based on the total remaining doses and automatically transmitting a purchase order to refile or reorder additional doses upon meeting the threshold.

7. A method for electronically tracking ingestible product consumption over a series of timed dosages, the method comprising:
   affixing, inserting or imprinting onto the interior of a product container a machine-readable optical code encoding an identifier unique to that individual container, the container enclosing an ingestible product wherein the optical code is only readable when the container is open and the product accessible;
   establishing a schedule of timed dosages for the product in a software application operable on a portable, network-connected electronic device;

decoding the machine-readable optical code through a camera in the device to resolve the machine-readable optical code back to the identifier;

registering a data association between the identifier and the schedule of timed dosages;

subsequently, scanning the machine-readable optical code upon administration of a scheduled dose by the device to decode the identifier from the machine-readable optical code;

automatically resolving both the product administered and schedule of timed dosages for that product from the prior damage association with the identifier;

storing a record of the scheduled dose timestamp whereby the software application updates a database for the schedule of timed dosages with the timestamp of the last scan of the machine-readable optical code decoded to the identifier;

initializing a quantity of doses upon the registering of the data association between the identifier and the schedule of timed dosages;

decrementing the quantity of doses upon each subsequent scan of the machine-readable optical code;

calculating the total remaining doses;

displaying on the device the total remaining doses, calculating the remaining time left on the schedule of timed dosages based on the total remaining doses and displaying on the device the total remaining time left taking the product according to the schedule of timed dosages;

establishing a database query that returns records for the schedule of doses when in an overdue state;

polling the database query to retrieve records for one or more overdue doses; and firing a notification event to alert one or more recipients of the overdue state whereby the one or more recipients are notified to administer the dose of product.

* * * * *